United States Patent [19]
Gamblin et al.

[11] Patent Number: 5,962,370
[45] Date of Patent: Oct. 5, 1999

[54] HERBICIDAL COMPOSITIONS COMPRISING A 4-BENZOYLISOXAZOLE AND A TRIAZINE HERBICIDE

[75] Inventors: Alan Gamblin; Vladir Cezarino; Richard Henry Hewett, all of Ongar, United Kingdom; Takashi Nishida, deceased, late of Sao Paulo, Brazil, by Vera Lúcia Boiago Nishida, Flávio Nishida, Thiago Nishida, executors

[73] Assignee: Rhone-Poulenc Agriculture Ltd, Ongar, United Kingdom

[21] Appl. No.: 08/915,331

[22] Filed: Aug. 20, 1997

Related U.S. Application Data

[62] Continuation of application No. 08/768,136, Dec. 17, 1996, abandoned, which is a continuation of application No. 08/656,228, filed as application No. PCT/EP94/04052, Dec. 6, 1994, abandoned.

[30] Foreign Application Priority Data

Dec. 10, 1993 [GB] United Kingdom .................. 9325284

[51] Int. Cl.[6] ...................... A01N 43/70; A01N 43/707; A01N 43/80
[52] U.S. Cl. ............................................. 504/134
[58] Field of Search ............................................. 504/134

[56] References Cited

U.S. PATENT DOCUMENTS 5,371,064  12/1994  Cramp et al. .......................... 504/271

FOREIGN PATENT DOCUMENTS

| | | |
|---|---|---|
| 0418175 | 3/1991 | European Pat. Off. . |
| 0487357 | 5/1992 | European Pat. Off. . |
| 0527036 | 2/1993 | European Pat. Off. . |
| 0527037 | 2/1993 | European Pat. Off. . |
| 0560482 | 9/1993 | European Pat. Off. . |
| 2 284 547 | 5/1995 | United Kingdom . |

OTHER PUBLICATIONS

*Chemical Abstracts*, vol. 121 (9), 1994, 10181g (Pollak et al).
Database WPI, Section C, Week 8402, 1984, abstract No. 84–006056/02 (abstract of CA 1158058).
*The Pesticide Manual*, ninth edition, British Crop Protection Council, ed. Worthing et al, 1991, pp. 26, 41–42, 47, 192–193, 573, 589, 710–711, 763–765, 797–800, 848.
Limpel et al, *1 Proc. NEWCC*, vol. 116, pp. 48–53 (1962).
Tammes et al, *Netherlands Journal of Plant Pathology*, 70, pp. 73–80 (1964).

*Primary Examiner*—S. Mark Clardy
*Attorney, Agent, or Firm*—Burns, Doane, Swecker & Mathis, L.L.P.

[57] ABSTRACT

The invention relates to compositions comprising a 4-benzoylisoxazole derivative of formula (I), wherein R, $R^1$, $R^2$ and n are as defined in the description, and a triazine herbicide, and their use as herbicides.

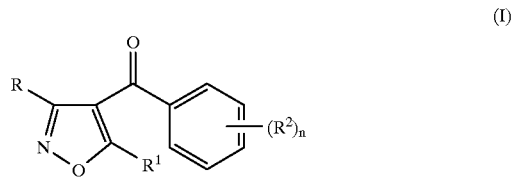

(I)

35 Claims, 8 Drawing Sheets

HERBICIDAL COMPOSITIONS COMPRISING A 4-BENZOYLISOXAZOLE AND A TRIAZINE HERBICIDE

CROSS-REFERENCE TO RELATED APPLICATIONS

This application is a continuation of U.S. patent application Ser. No. 08/768,136, filed Dec. 17, 1996, abandoned which is continuation of U.S. patent application Ser. No. 08/656,228, filed Jun. 10, 1996, abandoned, which was filed under 35 USC 371 as the U.S. national phase of International Application No. PCT/EP94/04052, filed Dec. 6, 1994, which designated the United States.

The present invention relates to new herbicidal compositions comprising a mixture of 1,3,5-triazine or 1,2,4-triazinone herbicides and 4-benzoylisoxazole derivatives, and to their use in agriculture.

The above compounds are already known in the art as herbicides. 1,3,5-Triazine and 1,2,4-triazinone herbicides (hereinafter referred to as the triazine herbicides) include ametryn ($N^2$-ethyl-$N^4$-isopropyl-6-methylthio-1,3,5-triazine-2,4-diamine), atrazine (6-chloro-$N^2$-ethyl-$N^4$-isopropyl-1,3,5-triazine-2,4-diamine, aziprotryne (4-azido-N-isopropyl-6-methylthio-1,3,5-triazin-2-ylamine), cyanazine [2-(4-chloro-6-(ethylamino)-1,3,5-triazin-2-ylamino)-2-methylpropionitrile], methoprotryne [$N^2$-isopropyl-$N^4$-(3-methoxypropyl)-6-methylthio-1,3,5-triazine-2,4-diamine], metribuzin (4-amino-6-tert-butyl-3-methylthio-1,2,4-triazin-5(4H)-one), prometryn ($N^2$, $N^4$-di-isopropyl-6-methylthio-1,3,5-triazine-2,4-diamine), prometon ($N^2$,$N^4$-di-isopropyl-6-methoxy-1,3,5-triazine-2,4-diamine), propazine (6-chloro-$N^2$,$N^4$-di-isopropyl-1,3,5-triazine-2,4-diamine), simetryn ($N^2$,$N^4$-diethyl-6-methylthio-1,3,5-triazine-2,4-diamine), simazine (6-chloro-$N^2$,$N^4$-diethyl-1,3,5-triazine-2,4-diamine), terbuthylazine ($N^2$-tert-butyl-6-chloro-$N^4$-ethyl-1,3,5-triazine-2,4-diamine), terbutryn ($N^2$-tert-butyl-$N^4$-ethyl-6-methylthio-1,3,5-triazine-2,4-diamine) and trietazine (6-chloro-$N^2$,$N^2$,$N^4$-triethyl-1,3,5-triazine-2,4-diamine), and are disclosed for example in "The Pesticide Manual", 9th edition (British Crop Protection Council) as selective herbicides. Herbicidal 4-benzoylisoxazoles of formula I below are disclosed in European Patent Publication Numbers 0418175, 0487357, 0527036 and 0560482.

As a result of research and experimentation is has been found that the use of a triazine herbicide, in combination with certain 4-benzoylisoxazole derivations, extends the spectrum of herbicidal activity without loss of crop selectivity. Therefore the said combinations represents an important technological advance. The term "combination" as used in this specification refers to the term "combination" as used in this specification refers to the "combination" of a 4-benzoylisoxazole herbicide and a triazine herbicide.

Surprisingly, in addition to this, it has been found that the combined herbicidal activity of certain 4-benzoylisoxazoles with triazine herbicide for the control of certain weed species, including *Brachiara plantaginea, Echinochloa crus-galli, Bidens pilosa, Cassia occidentalis, Ipomoea aristolochiaefolia, Euphorbia heterophylla, Setaria spp, Abutilon theophrasti, Amaranthus retroflexus, Ipomoea purpurea, Sida spinosa, Xanthium strumarium* and *Digitaria sanguinalis* is greater than expected, without an unacceptable increase in crop phytotoxicity, applied pre- or post-emergence (e.g. as a pre- or post-emergence aqueous spray), i.e. the herbicidal activity of the 4-benzoylisoxazole with a triazine herbicide showed an unexpected degree of synergism, as defined by Limpel, L. E., P. H. Schuldt and D. Lamont, 1962. 1.Proc.NEWCC 16, 48–53, using the formula:

$$E = X + Y - \frac{X \cdot Y}{100}$$

where

E=the expected percent inhibition of growth by a mixture of two herbicides A and B at defined doses.

X=the percent inhibition of growth by herbicide A at a defined dose.

Y=the percent inhibition of growth by herbicide B at a defined dose.

When the observed percentage of inhibition by the mixture is greater than the expected value E using the formula above the combination is synergistic.

The remarkable synergism on of certain combinations on *Brachiara plantaginea, Echinochloa, crus-galli, Bidens pilosa, Cassia occidentalis, Ipomoea aristolochiaefolia, Euphorbia heterophylla, Setaria spp, Abutilon theophrasti, Amaranthus retroflexus, Ipomoea purpurea, Sida spinosa, Xanthium strumarium* and *Digitaria sanguinalis* gives improved reliability in controlling these competitive weeds of many crop species, leading to a considerable reduction in the amount of active ingredient required for weed control.

A high level of control of these weeds is desirable to prevent:

1) yield loss, through competition and/or difficulties with harvest,
2) crop contamination leading to storage and cleaning difficulties, and
3) unacceptable weed seed return to the soil.

Accordingly the present invention provides a method for controlling the growth of weeds (i.e. undesired vegetation) at a locus which comprises applying to the locus:

(a) a 4-benzoylisoxazole derivative formula I:

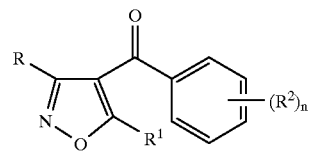

(I)

wherein

R is hydrogen or —$CO_2R^3$;

$R^1$ is cyclopropyl;

$R^2$ is selected from halogen (preferably chlorine or bromine), —$S(O)_p$Me and $C_{1-6}$ alkyl or haloalkyl (preferably trifluoromethyl), n is two or three; p is zero, one or two; and $R^3$ is $C_{1-4}$ alkyl; and (b) a triazine herbicide.

For this purpose, the 4-benzoylisoxazole and triazine herbicide are normally used in the form of herbicidal compositions (i.e. in association with a herbicidially acceptable diluent or carrier and/or surface active agent), for example as hereinafter described.

Preferably the triazine herbicide is a compound of formula II:

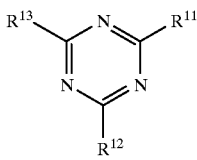

wherein $R^{11}$ represents chlorine or straight- or branched chain alkylthio or alkoxy having from one to six carbon atoms, $R^{12}$ represents azido, monoalkylamino, dialkylamino or cycloalkyamino, in which the alkyl or cycloalkyl moieties may be optionally substituted by one or more substituents selected from cyano and alkoxy; and $R^{13}$ represents straight- or branched- chain N-alkylamino having from one to six carbon atoms;

or of formula III:

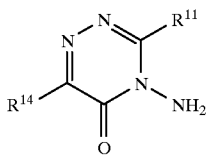

wherein $R^{14}$ represents straight- or branched chain alkyl having from one to six carbon atoms.

More preferably $R^{11}$ represents chlorine or methylthio and $R^{13}$ represents straight- or branched- chain N-alkylamino having from one to four carbon atoms.

Compositions containing compounds of formula II above wherein $R^{12}$ represents azido, straight- or branched- chain N-alkylamino having from one to four carbon atoms (wherein the alkyl moiety is optionally substituted by cyano or methoxy) are preferred.

Further preferred compounds of formula II above are those in which $R^{13}$ represent N-(t-butyl)amino, $R^{12}$ represents N-ethylamino and $R^{11}$ represents chlorine or methylthio, which are known respectively as terbuthylazine and terbutryn.

Preferred compounds of formula II above are those in which $R^{11}$ represents chlorine, $R^{13}$ represents N-ethylamino and $R^{12}$ represents N-ethylamino, N-(2-methylpropanenitrile)amino or N-isopropylamino, known respectively as simazine, cyanazine and atrazine, cyanazine and atrazine being most preferred.

A preferred compound of formula III above is the compound in which $R^{11}$ represents methylthio, $R^{14}$ represents tert-butyl, which is known as metribuzin.

In formula I above, preferably one of the groups $R^2$ is $—S(O)_p Me$.

In formula I above, compounds in which n is three and the groups $(R^2)_n$ occupy the 2,3 and 4-positions of the benzoyl ring; or in which n is two and the groups $(R^2)_n$ occupy and the 2 and 4- positions of the benzoyl ring are preferred.

In formula I above, preferably $(R^2)_n$ is $2-SO_2Me-4-CF_3$, $2-CF_3-4-SO_2Me$, $2-Cl-4-SO_2Me$, $2-SO_2Me-4-Br$, $2-SO_2Me-4-Cl$ or 2-SMe-3,4-dichloro.

Particularly preferred compounds of formula I include the following:

A 5-cyclopropyl-4-(2-methylsulphonyl-4-trifluoromethyl)benzoylisoxazole;

B 5-cyclopropyl-4-(4-methylsulphonyl-2-trifluoromethyl)benzoylisoxazole;

C 4-(2-chloro-4-methylsulphonyl)benzoyl-5-cyclopropylisoxazole;

D 4-(4-chloro-2-methylsulphonyl)benzoyl-5-cyclopropylisoxazole;

E 4-(4-bromo-2-methylsulphonyl)benzoyl-5-cyclopropylisoxazole;

F ethyl 3-[5-cyclopropyl-4-(3,4-dichloro-2-methylsulphenyl)benzoylisoxazole]carboxylate; and G 5-cyclopropyl-4-(3,4-dichloro-2-methylsulphonyl)benzoylisoxazole.

The letters A to G are assigned to these compounds for reference and identification hereafter.

Compounds A and F are particularly preferred.

The amounts of the triazine herbicide and 4-benzoylisoxazole applied vary depending on the the weeds present and their population, the composition is used, the timing of the application, the climatic and edaphic conditions, and (when used to control the growth of weeds in crop growing areas) the crop to be treated. In general, taking these factors into account, application rates from 5 g to 500 g of 4-benzoylisoxazole and from 250 g to 5000 g of the triazine herbicide per hectare give good results. However, it will be understood that higher or lower application rates may be used, depending upon the problem of weed control encountered.

For the selective control of weeds at a locus of weed infestation which is an area used, or to be used, for growing of crops application rates from 5 g to 500 g of 4-benzoylisoxazole and from 250 g to 5000 g of the triazine herbicide per hectare are particularly suitable, preferably from 25 to 150 g of 4-benzoylisoxazole and from 500 g to 1500 g of the triazine herbicide per hectare. When applied to a crop-growing area, the rate of application should be sufficient to control the growth of weeds without causing substantial permanent damage to the crop.

According to a further feature of the present invention there is provided a method of controlling the growth of weeds at a locus which comprises the the combined use of (a) 4-benzoylisozaxole of formula I as defined above; and
(b) a triazine herbicide;

by pre- or post- emergence application.

The combined use described above may be used to control a very wide spectrum of annual broad-leafed weeds and grass weeds in crops, e.g. maize, plantatation crops such as sugar cane, without significant permanent damage to the crop. The combined use described above offers both foliar and residual activity and consequently can be employed over a long period of crop development, i.e. from pre-weed pre-crop emergence to post-weed post-crop emergence.

In the method according to this feature of the present invention the combined use of (a) and (b) to control grass weeds in maize is preferred.

Where the triazine herbicide is ametryn the combined use of (a) and (b) to control grass weeds in sugar cane is also preferred.

Preferably the herbicides are applied pre-emergence of the weeds. Where the compound of formula (I) is Compound F above, post-emergence application is preferred.

In the method described above, the combined use of (a) and (b) in proportions of 2:1 to 1:1000 wt/wt of (a):(b) is preferred, proportions of 1:3.3 to 1:60 wt/wt being particularly preferred.

By the term 'pre-emergence application' is meant application to the soil in which the weed seeds or seedlings are present before emergence of the crop. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil, are controlled.

In accordance with the usual practice, a tank mix may be prepared prior to use by combining separate formulations of the individual herbicidal components.

The following non-limiting experiments illustrate the present invention.

GENERAL EXPERIMENTAL PROCEDURE

Experiment A

The experiments were carried out pre-emergence of the weed species at a research farm in Brazil. Compound A (formulated as a wettable powder) and atrazine were weighed out and dissolved in water to give a solution containing the appropriate concentrations and ratios of active ingredients.

The solution was mixed for one hour and applied at a spray volume of 231 liters/hectare to a 3 meter test plot comprising the weed species which were sown 2 days earlier. 3 replicates were performed. A control plot was sprayed with a solution not containing test compound. Visual assessment of phytotoxicity was made after 36 days from sowing each weed species based on a comparison with the control plot.

The tables below show the observed percentage control of the weed species by each combination, with the figure in brackets representing the predicted value using the Limpel formula.

EXAMPLE A1

Trails showing the nature of the synergistic biological effect of the combination on *Brachiara plantaginea*

|          |            | Compound A |         |         |
|----------|------------|------------|---------|---------|
|          | g (a.i.)/ha | 0          | 74      | 100     |
| Atrazine | 0          | —          | 77      | 87      |
|          | 1250       | 10         | 95 (79) | 95 (88) |

EXAMPLE A2

Trial demonstrating the nature of the synergistic biological effect of the combination on *Echinochloa crus-galli*

|          |            | Compound A |         |         |
|----------|------------|------------|---------|---------|
|          | g (a.i.)/ha | 0          | 74      | 100     |
| Atrazine | 0          | —          | 77      | 88      |
|          | 1250       | 27         | 95 (83) | 97 (91) |

EXAMPLE A3

Trial demonstrating the nature of the synergistic biological effect of the combination on *Bidens pilosa*

|          |            | Compound A |         |         |
|----------|------------|------------|---------|---------|
|          | g (a.i.)/ha | 0          | 74      | 100     |
| Atrazine | 0          | —          | 35      | 67      |
|          | 1250       | 70         | 87 (81) | 95 (90) |

EXAMPLE A4

Trial demonstrating the nature of the synergistic biological effects of the combination on *Cassia occidentalis*

|          |            | Compound A |         |         |
|----------|------------|------------|---------|---------|
|          | g (a.i.)/ha | 0          | 74      | 100     |
| Atrazine | 0          | —          | 5       | 37      |
|          | 1250       | 25         | 77 (29) | 85 (53) |

EXAMPLE A5

Trial demonstrating the nature of the synergistic biological effect of the combination on *Ipomoea aristolochiaefolia*

|          |            | Compound A |         |         |
|----------|------------|------------|---------|---------|
|          | g (a.i.)/ha | 0          | 74      | 100     |
| Atrazine | 0          | —          | 5       | 33      |
|          | 1250       | 52         | 88 (54) | 96 (68) |

EXAMPLE A6

Trial demonstrating the nature of the synergistic biological effect of the combination of *Euphorbia heterophylla*

|          |            | Compound A |         |         |
|----------|------------|------------|---------|---------|
|          | g (a.i.)/ha | 0          | 74      | 100     |
| Atrazine | 0          | —          | 5       | 27      |
|          | 1250       | 23         | 82 (27) | 87 (44) |

Experiment B

The experiments were carried out pre-emergence of the weed species at a research farm in Washington state, USA. Compound B (formulated as a wettable powder) and atrazine (formulated as a suspension concentrate) were weighed out and dissolved in water to give a solution containing the appropriate concentrations and ratios of active ingredients.

The solution was mixed for one hour and applied at a spray volume of 231 liters/hectare to a 3 meter by 5 meter test plot comprising the weed species which were sown 2 days earlier. 3 replicates were performed. A control plot was sprayed with a solution not containing test compound. Visual assessment of phytotoxicity was made after 42 days from sowing each weed species based on a comparison with the control plot.

The tables below show the observed percentage control of the weed species by each combination, with the figure in brackets representing the predicted value using the Limpel formula.

EXAMPLE B1

Trial demonstrating the nature of the synergistic biological effect of the combination of *Setaria faberi*

|  |  | Compound B | |
|---|---|---|---|
| g (a.i.)/ha |  | 0 | 50 |
| Atrazine | 0 | — | 68 |
|  | 1000 | 87 | 100 (96) |

With reference to the formula given at the beginning of the description, the results above clearly demonstrate the excellent and unexpected degree of synergism obtained with the combination of the invention.

It will be understood that the results presented above were all obtained in field trials. Such trials generally represent a more rigorous test of herbicidal properties than tests in the greenhouse, where test plants are protected from the variable conditions to which they are inevitably subject in the open field. Because of the variability of conditions in field tests, it is generally more difficult to secure a clear showing of synergism than in greenhouse testing. Nevertheless, herbicidal mixtures which demonstrate synergism in greenhouse testing must, if they are to be of commercial utility, be capable of demonstrating synergism under field conditions, i.e. under the conditions which will prevail when they are used by a farmer. The results obtained in the foregoing Examples therefore represent a particularly clear demonstration of synergism under practical conditions.

Experiment C

The following experiments were carried out using Compound A in mixtures with various triazine herbicides (atrazine and cyanazine). Seed of the various species of broad-leaf or grass weeds were sown in unsterilised clay loam soil in 7 centimeter by 7 centimeter plastic plant pots. The pots were watered and allowed to drain. The soil surface was then sprayed with ranges of concentrations of either the individual herbicide or mixtures of two herbicides (compound A and atrazine as technical material; cyanazine as the commercially available formulation "Fortrol", trade mark, which is a suspension concentrate) in various proportions, dissolved in a 50:50 by volume solution of acetone and water, using a track sprayer set to deliver the equivalent of 290 l/ha. The herbicides were used as unformulated technical materials.

Treated pots were placed at random in four replicate blocks per treatment for each plant species. The pots were held, in a glasshouse, standing on moist capillary matting, under lights and with overhead watering twice daily.

Two weeks after treatment the percent reduction in plant growth, compared to an untreated control, was assessed.

Mean percent reduction in plant growth was calculated for each treatment. Dose/mean response was plotted on Log concentration/Probability graph paper, and lines fitted by eye. For herbicide mixtures a dose/response line for the first herbicide was drawn for each dose rate of the second herbicide and a dose/response line for the second herbicide was drawn for each dose rate of the first herbicide. The doses representing a 90% reduction in plant growth (LD90 values) were read from these lines and plotted on graphs whose axes were dose rates of the two herbicides. The line joining these points is an Isobole i.e. a line joining points (mixtures) of equal activity, as described by P.M.L. Tammes, Neth. J. Plant Path. 70 (1964):73–80. A line was also drawn joining the LD90 values of the individual components of the mixture. This line represents the theoretical isobole if the effect of the two components is additive i.e. there is no interaction between them. Isoboles falling below this line indicate synergy between the components while lines laying above it indicate antagonism.

In the tables that follow 'dose' represents the dose rate in grammes per hectare of the active ingredient used; and the figures for the weed control are percentages reduction in growth when compared with the untreated controls.

EXAMPLE C1

Pre-emergence treatment of *Abutilon theophrasti* with various mixtures of Compound A and atrazine

|  |  | Atrazine | | | | | | |
|---|---|---|---|---|---|---|---|---|
| Cpd A | Dose g/ha | 0 | 31.25 | 62.5 | 125 | 250 | 500 | 1000 |
|  | 0 | — | 25 | 51.25 | 75 | 87.5 | 93.75 | 100 |
|  | 1 | 40 | 45 | 95 | 100 | 87.5 | 100 | 100 |
|  | 2 | 46.25 | 62.5 | 77.5 | 75 | 97.5 | 100 | 100 |
|  | 4 | 20 | 66.25 | 75 | 90 | 87.5 | 100 | 100 |
|  | 8 | 75 | 68.75 | 62.5 | 81.25 | 93.75 | 100 | 100 |
|  | 16 | 91.25 | 97.5 | 100 | 100 | 100 | 93.75 | 100 |
|  | 32 | 88.75 | 100 | 97.5 | 100 | 80 | 100 | 100 |
|  | 64 | 98.75 | 100 | 100 | 93.75 | 98.75 | 100 | 100 |
|  | 128 | 100 | 100 | 100 | 93.75 | 100 | 100 | 91.25 |
|  | 256 | 97.5 | 100 | 100 | 100 | 100 | 100 | 97.5 |

EXAMPLE C2

Pre-emergence treatment of *Amaranthus retroflexus* with various mixtures of Compound A and atrazine

|       |             | Atrazine |       |       |       |       |       |       |
|-------|-------------|-------|-------|-------|-------|-------|-------|-------|
| Cpd A | Dose g/ha   | 0     | 31.25 | 62.5  | 125   | 250   | 500   | 1000  |
|       | 0           | —     | 67.5  | 32.5  | 82.5  | 100   | 75    | 87.5  |
|       | 1           | 42.5  | 57.5  | 95    | 93.75 | 100   | 97.5  | 100   |
|       | 2           | 22.5  | 43.75 | 95    | 93.75 | 93.75 | 100   | 100   |
|       | 4           | 60    | 72.5  | 95    | 96.75 | 100   | 87.5  | 95    |
|       | 8           | 75    | 93.75 | 100   | 100   | 100   | 100   | 100   |
|       | 16          | 75    | 100   | 97.5  | 100   | 100   | 96.25 | 100   |
|       | 32          | 100   | 95    | 100   | 100   | 100   | 95    | 97.5  |
|       | 64          | 100   | 100   | 98.75 | 100   | 100   | 100   | 100   |
|       | 128         | 100   | 100   | 95    | 100   | 100   | 100   | 100   |
|       | 256         | 98.75 | 100   | 100   | 100   | 100   | 100   | 100   |

EXAMPLE C3

Pre-emergence treatment of *Echinochloa crus-galli* with various mixtures of Compound A and atrazine

|       |           | Atrazine |       |       |       |       |       |       |       |
|-------|-----------|-------|-------|-------|-------|-------|-------|-------|-------|
| Cpd A | Dose g/ha | 0     | 31.25 | 62.5  | 125   | 250   | 500   | 1000  | 2000  |
|       | 0         | —     | 5     | 15    | 50    | 61.5  | 86.25 | 88.75 | 97.5  |
|       | 1         | 0     | 10    | 41.25 | 30    | 48.75 | 83.75 | 90    | 95    |
|       | 2         | 5     | 2.5   | 42.5  | 40    | 62.5  | 86.25 | 91.25 | 96.25 |
|       | 4         | 0     | 15    | 40    | 78.75 | 86.25 | 92.25 | 98.75 | 97.5  |
|       | 8         | 10    | 52.5  | 55    | 84.75 | 92.5  | 97.5  | 97.5  | 100   |
|       | 16        | 51.25 | 73.75 | 62.5  | 88.75 | 89.75 | 97.5  | 96.67 | 97.5  |
|       | 32        | 86.25 | 92.5  | 92.5  | 96.25 | 96.25 | 96.25 | 96.25 | 97.5  |
|       | 64        | 95    | 98.75 | 95    | 96    | 97.5  | 96.25 | 97.25 | 100   |
|       | 128       | 95    | 95    | 95    | 95    | 95    | 96.25 | 95    | 95    |
|       | 256       | 95    | 95    | 95    | 95    | 97.5  | 95    | 97.5  | 95    |

EXAMPLE C4

Pre-emergence treatment of *Ipomoea purpurea* with various mixtures of Compound A and atrazine

|       |           | Atrazine |       |       |       |       |       |       |       |
|-------|-----------|-------|-------|-------|-------|-------|-------|-------|-------|
| Cpd A | Dose g/ha | 0     | 31.25 | 62.5  | 125   | 250   | 500   | 1000  | 2000  |
|       | 0         | —     | 65    | 67.5  | 8625  | 92.5  | 93.75 | 97.5  | 100   |
|       | 1         | 28.75 | 26.25 | 85    | 98.5  | 96.25 | 95    | 82.5  | 97.5  |
|       | 2         | 47.5  | 41.25 | 68.75 | 95    | 100   | 98.75 | 100   | 100   |
|       | 4         | 37.5  | 80    | 92.5  | 88.75 | 98.75 | 92.5  | 97.5  | 100   |
|       | 8         | 47.5  | 30    | 86.25 | 97.5  | 100   | 97.5  | 100   | 100   |
|       | 16        | 37.5  | 71.25 | 83.75 | 91.25 | 97.5  | 95    | 85    | 95    |
|       | 32        | 53.75 | 90    | 95    | 95    | 97.5  | 100   | 100   | 92.5  |
|       | 64        | 67.5  | 78.75 | 96.67 | 97.5  | 97.5  | 99.75 | 93.75 | 100   |
|       | 128       | 70    | 95    | 100   | 100   | 100   | 100   | 95    | 98.75 |
|       | 256       | 91.25 | 98.75 | 96.25 | 100   | 97.5  | 97.5  | 100   | 100   |

EXAMPLE C5

Pre-emergence treatment of *Setaria viridis* with various mixtures of Compound A and atrazine

| | | Atrazine | | | | | | | |
|---|---|---|---|---|---|---|---|---|---|
| Cpd A | Dose g/ha | 0 | 31.25 | 62.5 | 125 | 250 | 500 | 1000 | 2000 |
| | 0 | — | 6.25 | 10 | 17.5 | 56.25 | 56.25 | 62.5 | 77.5 |
| | 1 | 7.5 | 0 | 10 | 0 | 62.5 | 80 | 72.5 | 97.5 |
| | 2 | 5 | 12.5 | 18.75 | 0 | 12.5 | 62.5 | 85 | 73.75 |
| | 4 | 25 | 25 | 15 | 0 | 28.75 | 30 | 68.75 | 95 |
| | 8 | 60 | 25 | 47.5 | 43.75 | 45 | 83.75 | 91.25 | 100 |
| | 16 | 68.75 | 36.25 | 61.25 | 60 | 73.75 | 95 | 100 | 97.5 |
| | 32 | 85 | 77.5 | 81.25 | 76.25 | 92.5 | 96.25 | 96.25 | 96.25 |
| | 64 | 97.5 | 65 | 80 | 100 | 73.75 | 93.75 | 100 | 99.75 |
| | 128 | 86.25 | 97.5 | 85 | 98.75 | 100 | 100 | 100 | 100 |
| | 256 | 98.75 | 100 | 95 | 98.75 | 98.75 | 98.75 | 98.75 | 100 |

EXAMPLE C6

Pre-emergence treatment of *Echinochloa crus-galli* with various mixtures of Compound A and cyanazine

| | | Cyanazine | | | | | | | |
|---|---|---|---|---|---|---|---|---|---|
| Cpd A | Dose g/ha | 0 | 31.25 | 62.5 | 125 | 250 | 500 | 1000 | 2000 |
| | 0 | — | 12.5 | 7.5 | 0 | 62.5 | 63.75 | 90 | 94.75 |
| | 1 | 13.75 | 2.5 | 10 | 7.5 | 52.5 | 92.5 | 98.5 | 97.5 |
| | 2 | 20 | 13.75 | 2.5 | 17.5 | 48.75 | 92.25 | 97.5 | 95 |
| | 4 | 22.5 | 5 | 25 | 55 | 63.75 | 97.25 | 96.25 | 100 |
| | 8 | 37.5 | 53.75 | 52.5 | 63.75 | 86.25 | 99.75 | 98.75 | 98.5 |
| | 16 | 73.75 | 70 | 77.5 | 88.75 | 90 | 99.75 | 100 | 99.75 |
| | 32 | 91.25 | 91.25 | 91.25 | 98.75 | 94.75 | 99.75 | 99.75 | 100 |
| | 64 | 98.5 | 100 | 100 | 96 | 100 | 99.5 | 99.75 | 99.5 |
| | 128 | 100 | 99.75 | 98 | 98.25 | 100 | 99.75 | 99.5 | 98.25 |
| | 256 | 99.25 | 98.25 | 99.75 | 99.25 | 99.5 | 99 | 98.25 | 99.25 |

EXAMPLE C7

Pre-emergence treatment of *Amaranthus retroflexus* with various mixtures of Compound A and cyanazine

| | | Cyanazine | | | | | | |
|---|---|---|---|---|---|---|---|---|
| A | Dose g/ha | 0 | 31.25 | 62.5 | 125 | 250 | 500 | 1000 |
| | 0 | — | 42.5 | 71.25 | 45 | 80 | 96.25 | 93.75 |
| | 1 | 57.5 | 50 | 67.5 | 83.75 | 95 | 91.25 | 98.75 |
| | 2 | 62.5 | 87.5 | 50 | 89.75 | 95 | 93.75 | 98.75 |
| | 4 | 55 | 90 | 87.5 | 97.5 | 97.5 | 95 | 99.75 |
| | 8 | 87.5 | 82.5 | 96.25 | 96.25 | 100 | 97.5 | 98.75 |
| | 16 | 91.25 | 90 | 99.5 | 97.5 | 99.75 | 100 | 98.75 |
| | 32 | 98.75 | 100 | 100 | 100 | 98.75 | 100 | 100 |
| | 64 | 97.5 | 100 | 100 | 100 | 98.75 | 99.75 | 98.75 |
| | 128 | 97.5 | 97.5 | 100 | 100 | 100 | 100 | 100 |
| | 256 | 100 | 100 | 100 | 98.75 | 100 | 100 | 98.75 |
| | 512 | 100 | 98.75 | 100 | 100 | 98.75 | 100 | 100 |

EXAMPLE C8

Pre-emergence treatment of *Ipomoea purpurea* with various mixtures of Compound A and cyanazine

| | Cyanazine | | | | | | |
|---|---|---|---|---|---|---|---|
| Cpd A | Dose g/ha | 0 | 31.25 | 62.5 | 125 | 250 | 500 | 1000 |
| | 0 | — | 0 | 0 | 3.75 | 78.75 | 98.75 | 100 |
| | 1 | 6.25 | 2.5 | 2.5 | 37.5 | 82.5 | 80 | 100 |
| | 2 | 6.25 | 17.5 | 7.5 | 47.5 | 47.5 | 98.75 | 100 |
| | 4 | 2.5 | 45 | 5 | 58.75 | 65 | 100 | 100 |
| | 8 | 6.25 | 36.25 | 28.75 | 52.5 | 72.5 | 98.5 | 99.75 |
| | 16 | 26.25 | 58.75 | 57.5 | 66.25 | 85 | 93.75 | 100 |
| | 32 | 25 | 52.5 | 70 | 96.25 | 87.5 | 97.5 | 96.25 |
| | 64 | 75 | 75 | 88.75 | 95 | 100 | 96.25 | 100 |
| | 128 | 77.5 | 78.75 | 91.25 | 96.25 | 100 | 98.75 | 100 |
| | 256 | 68.75 | 90 | 91.25 | 97.5 | 97.25 | 98.75 | 100 |
| | 512 | 96.25 | 92.5 | 92.5 | 97.25 | 100 | 100 | 100 |

BRIEF DESCRIPTION OF DRAWINGS

FIG. 7 is an LD90 isobole plot calculated from observed values (-•-) and a corresponding plot of expected additive values (dashed line) for a range of mixtures of Compound A with cyanazine against the weed species *Amaranthus retroflexus*, produced from the results shown in Table C7;

Figure 1:
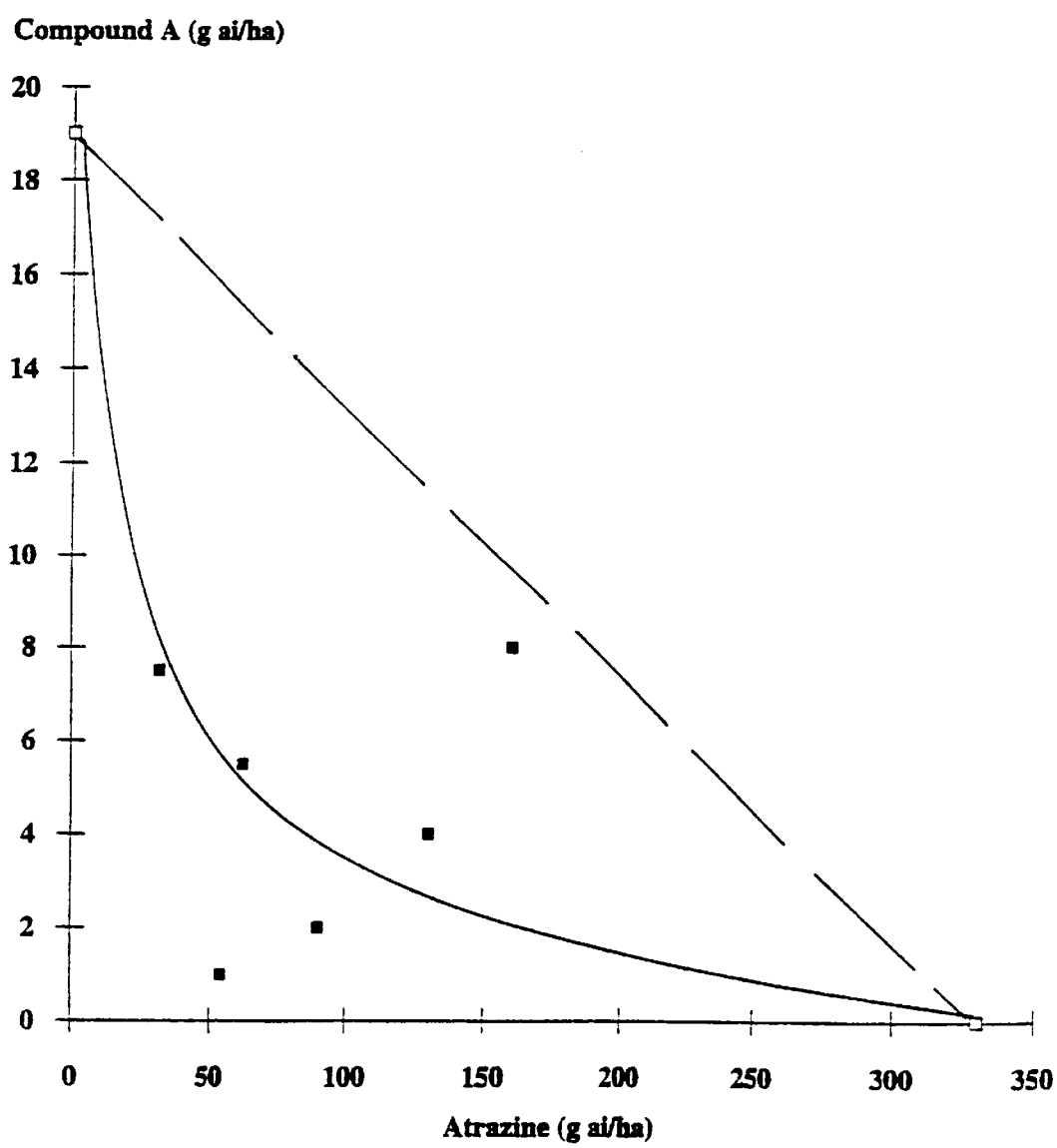
FIG. 1 is an LD90 isobole plot calculated from observed values (-•-) and a corresponding plot expected additive values (dashed line) for a range of mixtures of Compound A with atrazine against the weed species *Abutilon theophrasti*, produced from the results shown in Table C1.
Figure 2:
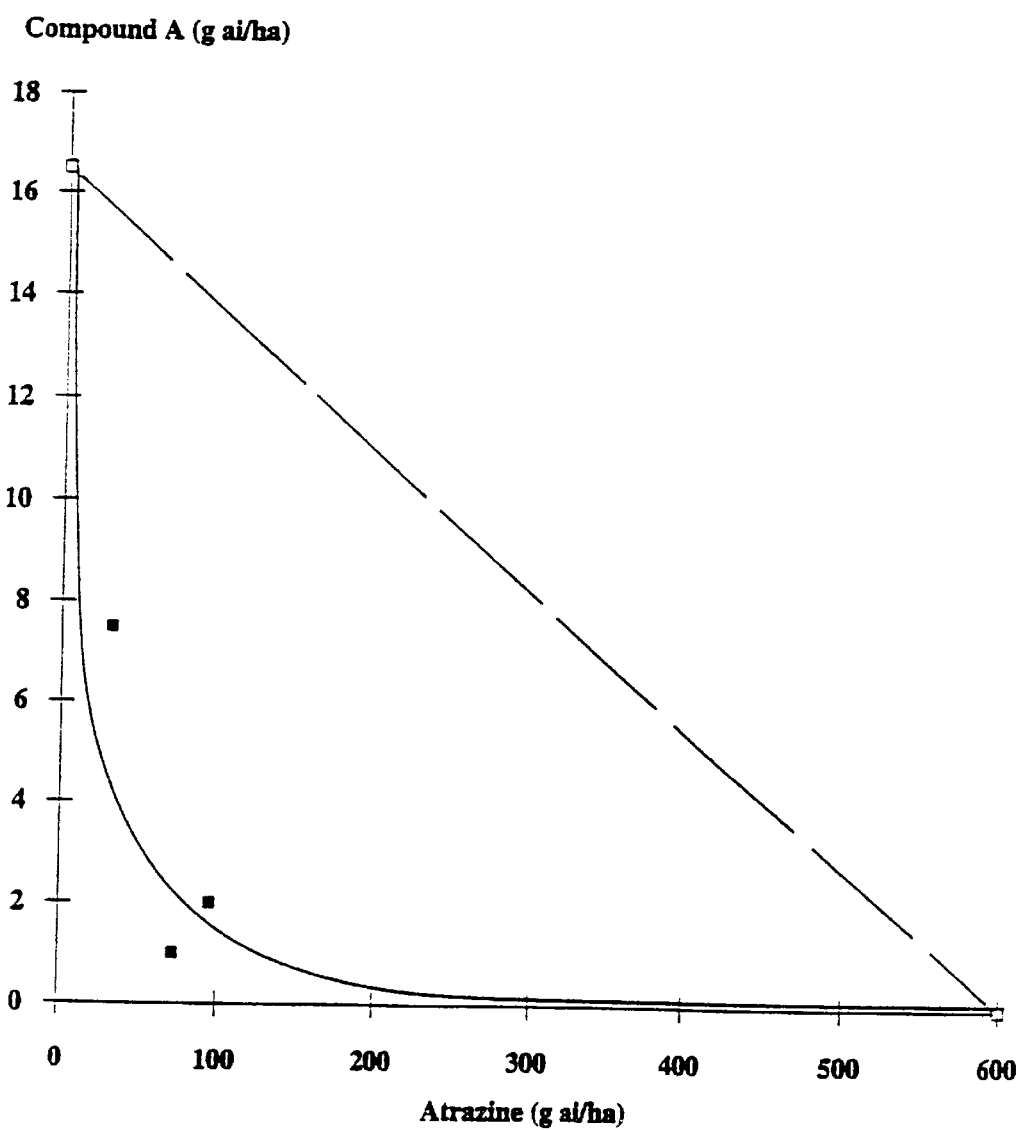
FIG. 2 is an LD90 isobole plot calculated from observed values (-•-) and a corresponding plot of expected additive values (dashed line) for a range of mixtures of Compound A with atrazine against the weed species *Amaranthus retroflexus*, produced from the results shown in Table C2.
Figure 3:
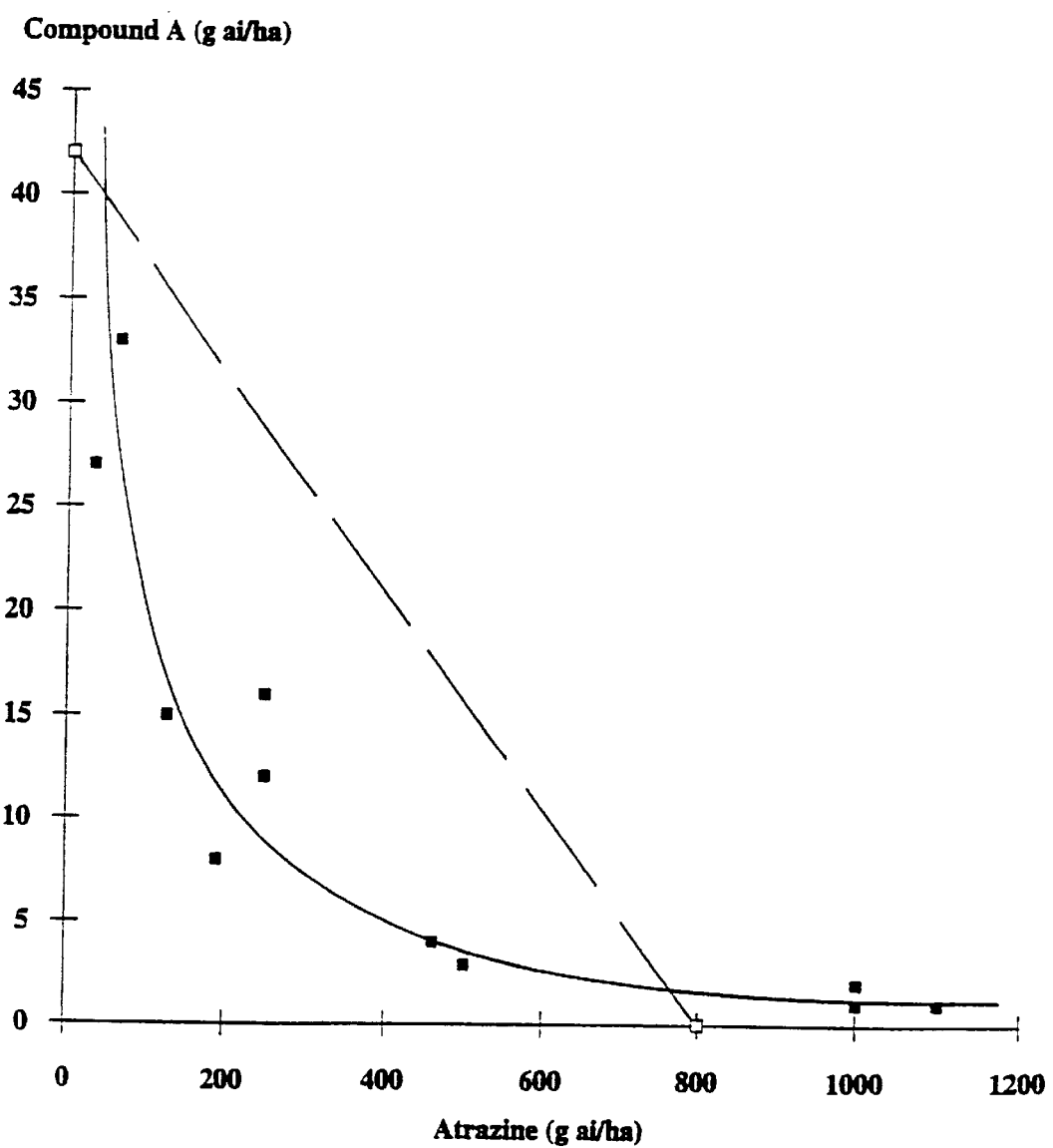
FIG. 3 is an LD90 isobole plot calculated from observed value (-•-) and a corresponding plot of expected additive values (dashed line) for a range of mixtures of Compound A with atrazine against the weed species *Echinochloa crus-galli*, produced from the results shown in Table C3.
Figure 4:
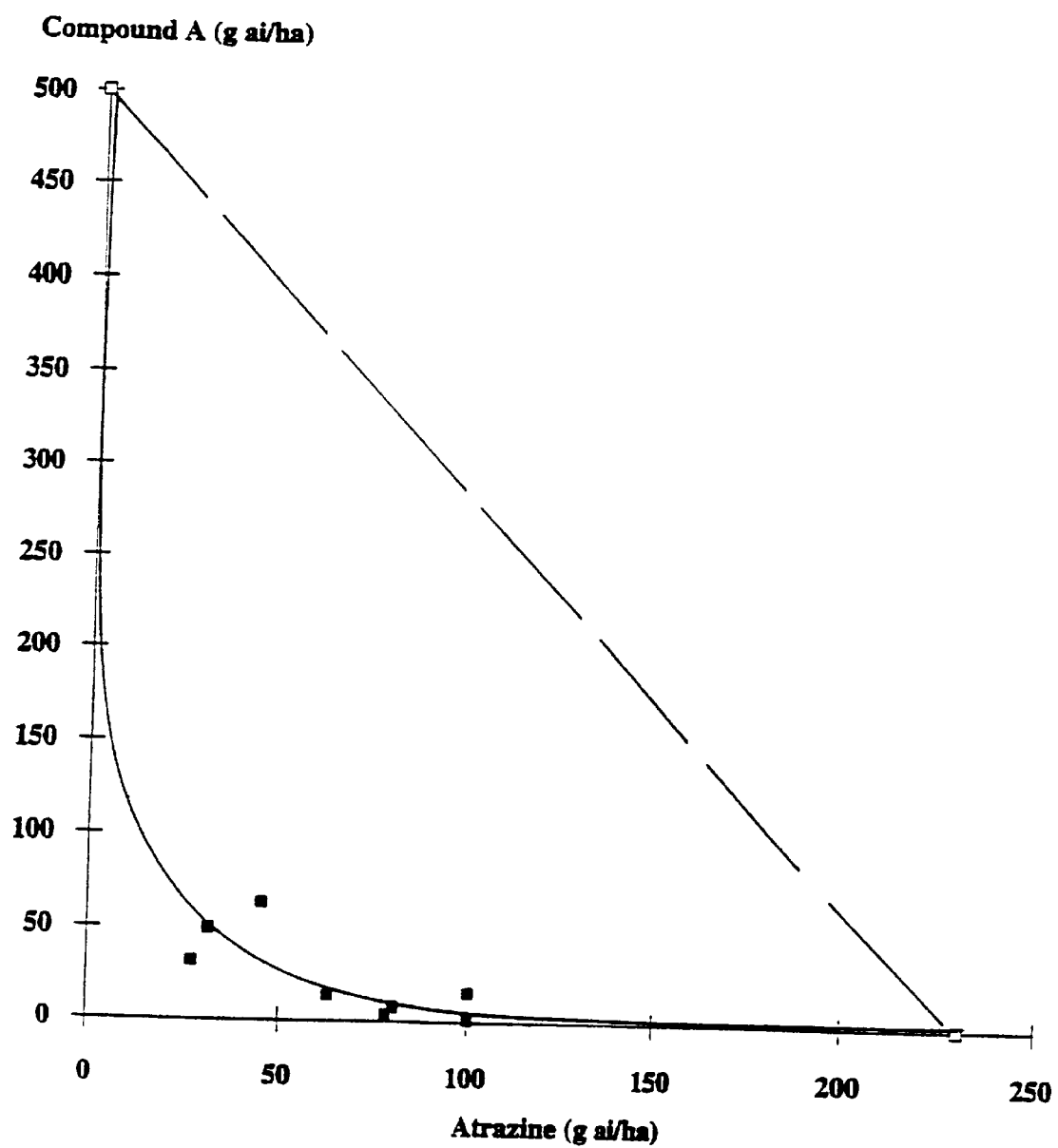
FIG. 4 is an LD90 isobole plot calculated from observed values (-•-) and a corresponding plot of expected additive values (dashed line) for a range of mixtures of Compound A with atrazine against the weed species *Ipomoea purpurea*, produced from the results shown in Table C4.
Figure 5:
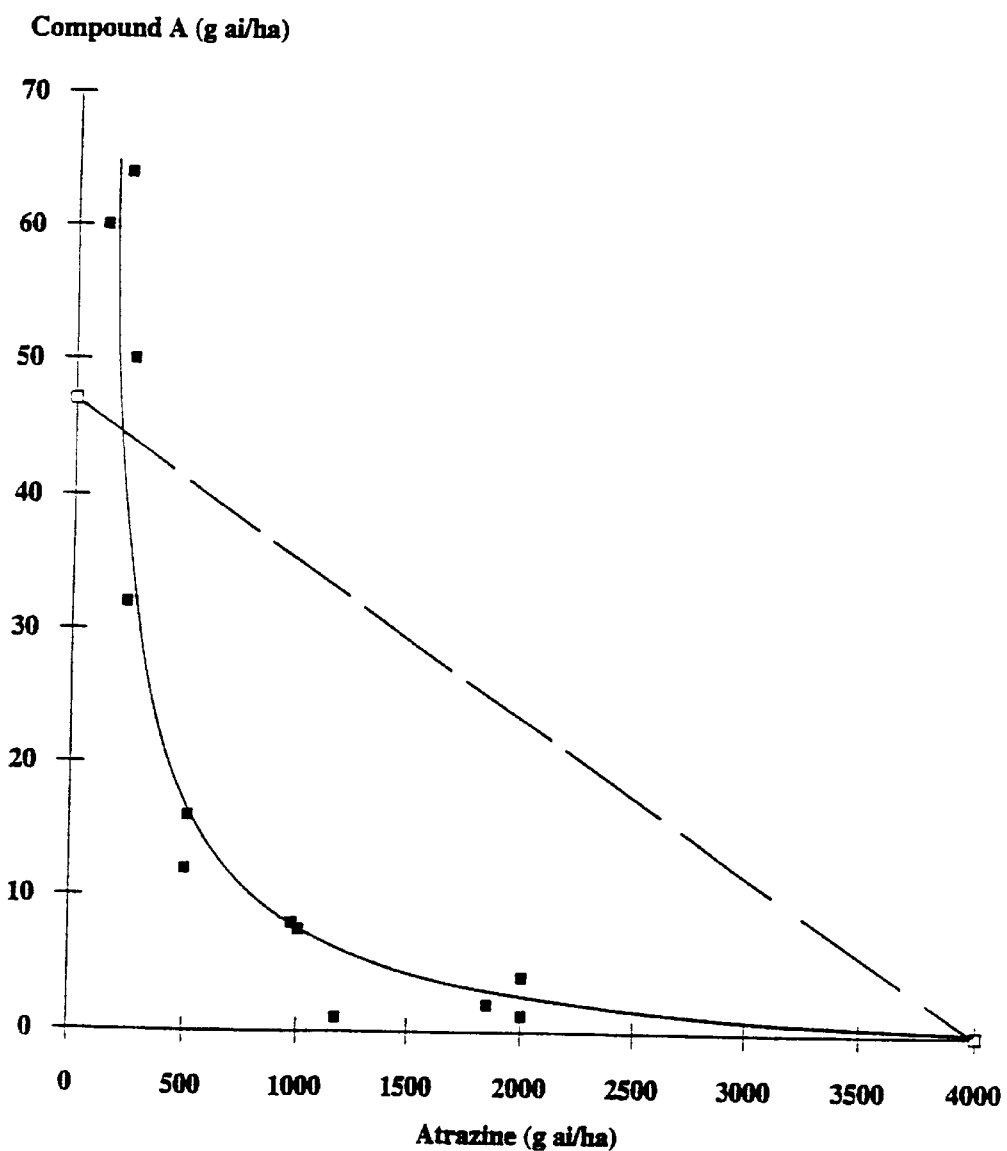
FIG. 5 is an LD90 isobole plot calculated from observed values (-•-) and a corresponding plot of expected additive values (dashed line) for a range of mixtures of Compound A with atrazine against the weed species *Setaria viridis*, produced from the results shown in Table C5.
Figure 6:
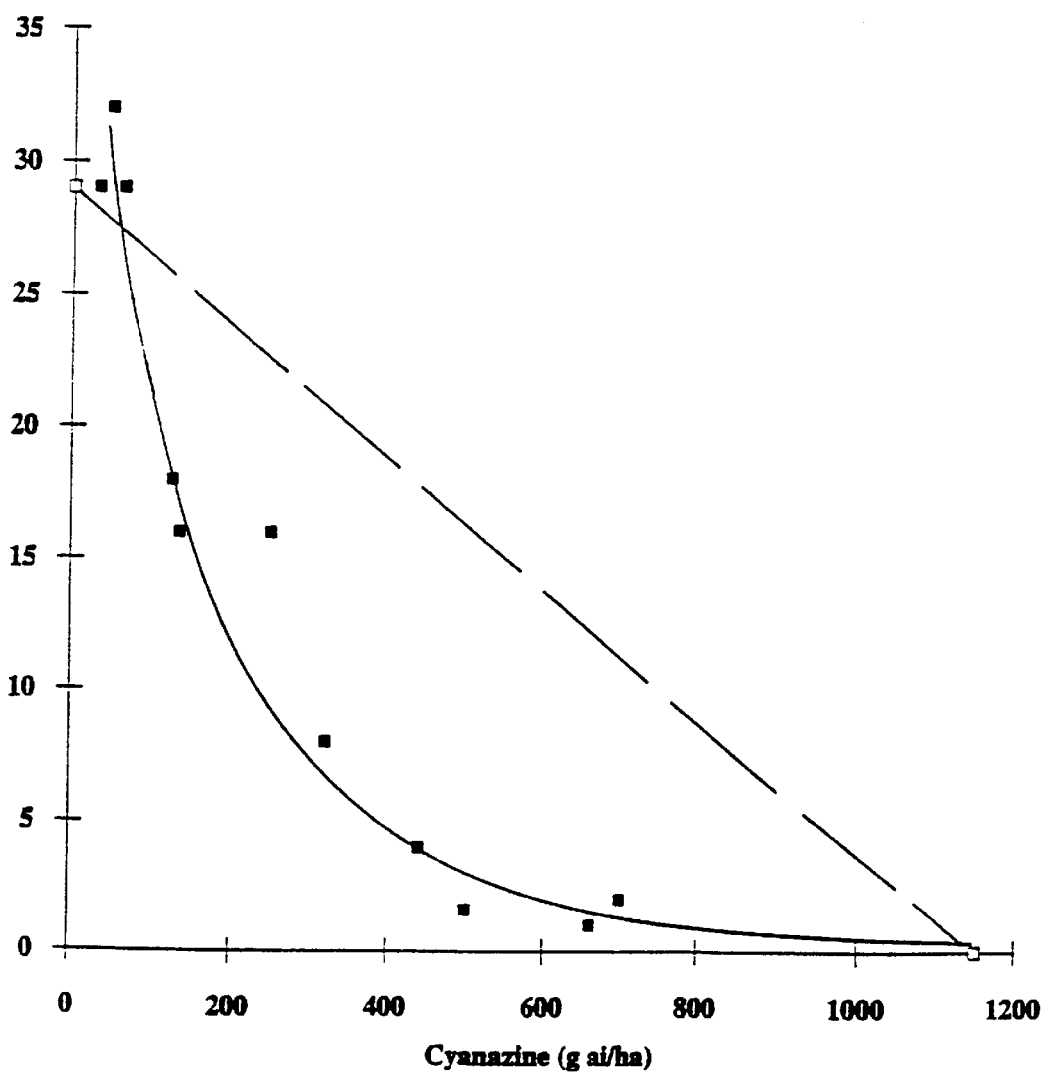
FIG. 6 is an LD90 isobole plot calculated from observed values (-•-) and a corresponding plot of expected additive values (dashed line) for a range of mixtures of Compound A with cyanazine against the weed species *Echinochloa crus-galli*, produced from the results shown in Table C6.
Figure 1:
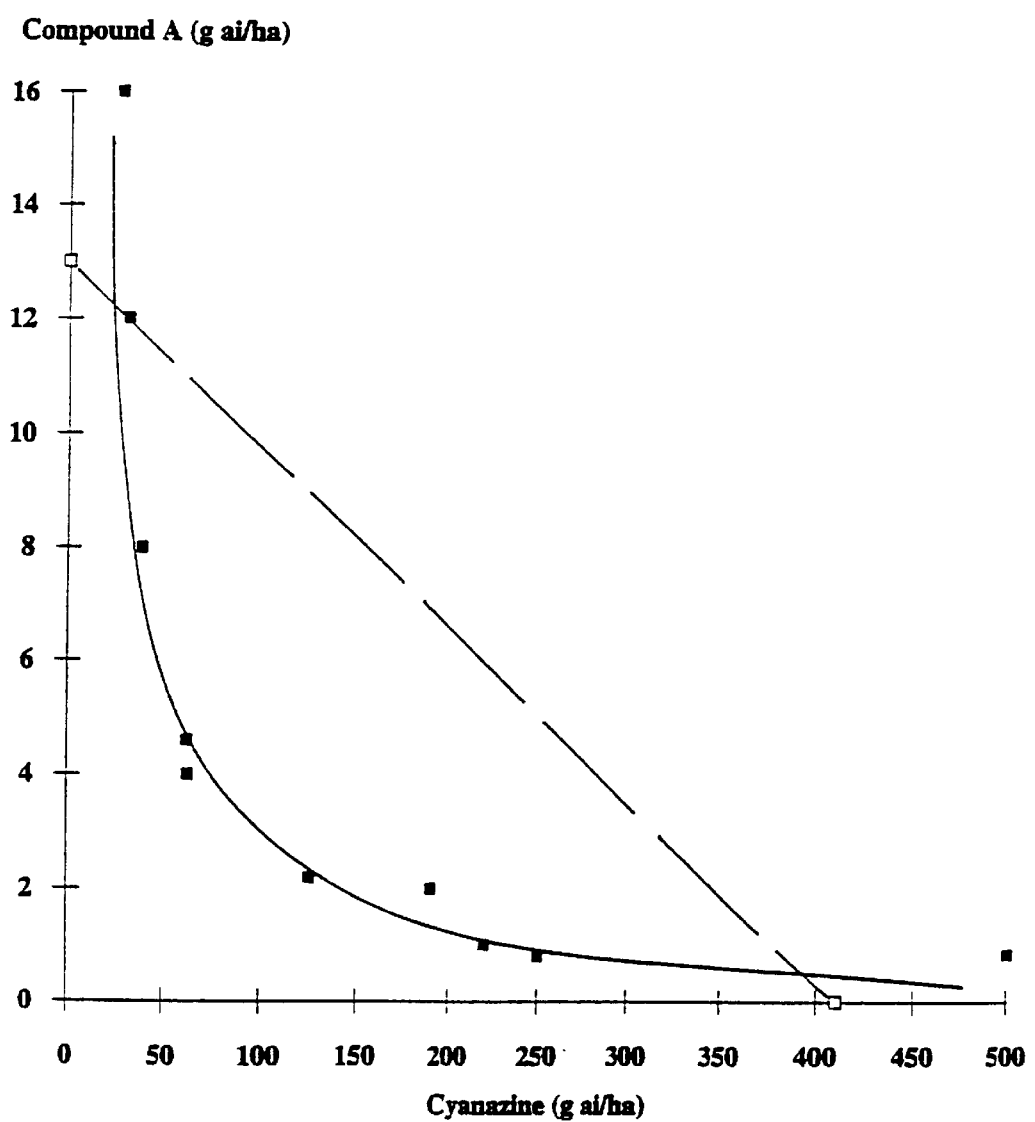
Figure 8:
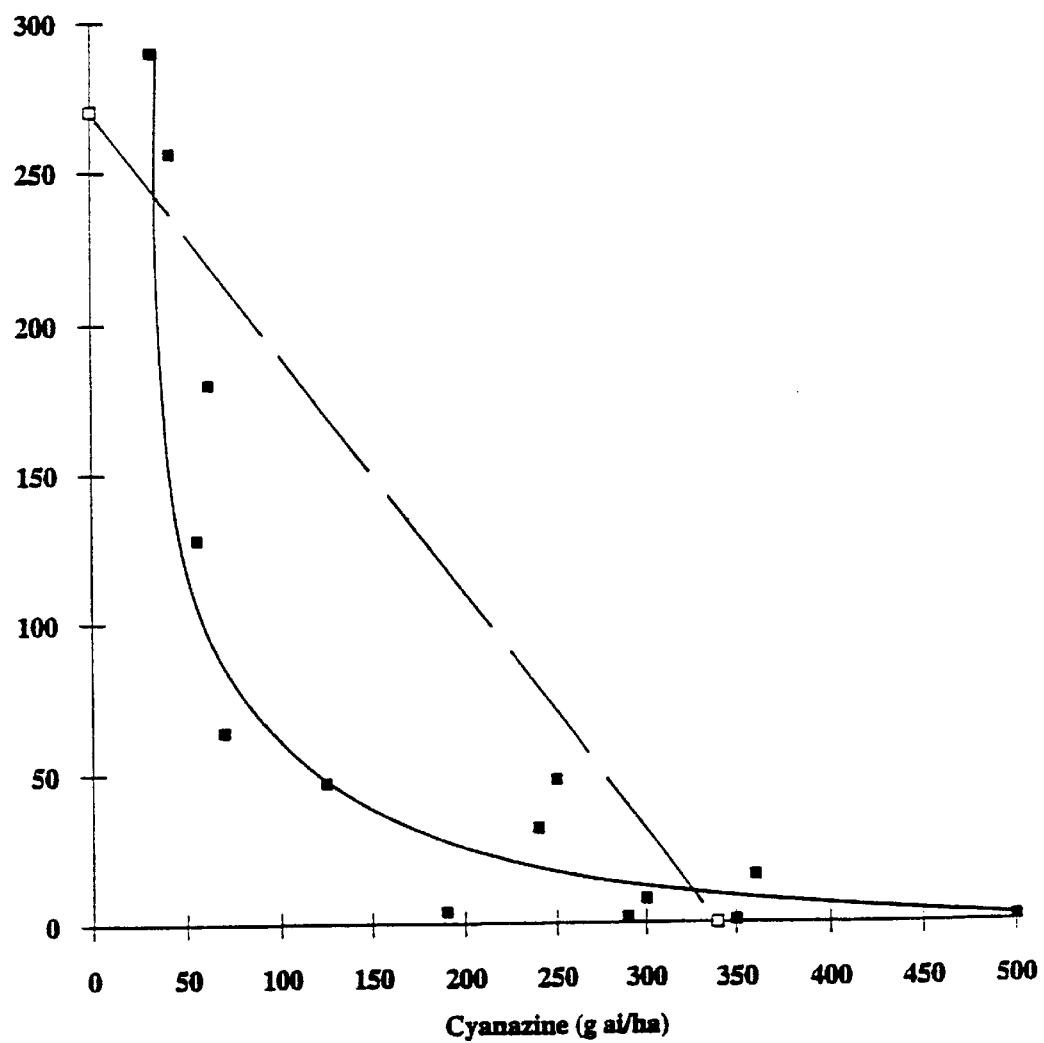
FIG. 8 is an LD90 isobole plot calculated from observed values (-•-) and a corresponding plot of expected additive values (dashed line) for a range of mixtures of Compound A with cyanazine against the weed species *Ipomoea purpurea*, produced from the results shown in Table C8.

The isoboles produced from the data in Example D1 to D8, shown hereinafter in FIGS. 1 to 8 respectively, were clearly type III curves (Tammes op. cit., Page 75, FIG. 2) characteristics of synergism.

Experiment D

The following experiments were conducted to demonstrate the post-emergence properties of mixtures comprising compound F (as a 50% wettable powder) and metribuzin (as a 70% water-dispersible granules, using the commercially available formulation "Sencor", trade mark). The two herbicides were made up in a solution containing 0.1% Agral (trade mark) and applied post-emergence both alone and in combination at a range of concentrations to the grass and broad-leaved weed species listed below. The spray jet (Model SS8003E) and pressure used (46 psi) gave a spray volume equivalent to 290 liters/ha. All plants were grown in non-sterile loam soil and treated at the following growth stages:

Broad-leafed weeds

*Ipomoea purpurea* 1 leaf

*Sida spinosa* 1–2 leaf

*Xanthium strumarium* 2+1 leaf

Grass Weeds

*Digitaria sanguinalis* 3 leaf

*Setaria viridis* 3 leaf

Treated plants were maintained on moist capillary matting under lights in a glasshouse. They received one overhead watering 24 hours after treatment and thereafter were sub-irrigated three times daily. Treatment effects were assessed visually 14 days after treatment. The percentage damage compared to untreated controls was recorded for each species.

The tables below show the observed percentage control of the weed species by each combination, with the figure in brackets representing the predicted value using the Limpel formula.

RESULTS

EXAMPLE D1

Post-emergence treatment of *Ipomoea purpurea* with various mixtures of Compound F and metribuzin

| | | Metribuzin | | | |
|---|---|---|---|---|---|
| | Dose g/ha | 0 | 32 | 63 | 125 |
| Cpd F | 0 | — | 0 | 0 | 20 |
| | 8 | 10 | 40 (10) | 60 (10) | 60 (28) |
| | 16 | 20 | 50 (20) | 50 (20) | 70 (36) |
| | 32 | 40 | 60 (40) | 65 (40) | 70 (52) |
| | 63 | 40 | 60 (40) | 70 (40) | 75 (52) |

EXAMPLE D2

Post-emergence treatment of *Sida spinosa* with various mixtures of Compound F and metribuzin

| | | Metribuzin | | |
|---|---|---|---|---|
| | Dose g/ha | 0 | 16 | 32 |
| Cpd F | 0 | — | 20 | 30 |
| | 8 | 0 | 30 (20) | 70 (30) |

EXAMPLE D3

Post-emergence treatment of *Xanthium strumarium* with various mixtures of Compound F and metribuzin

|  |  | Metribuzin | | | |
|---|---|---|---|---|---|
|  | Dose g/ha | 0 | 16 | 32 | |
|  |  | 16 | 40 | 70 (52) | 85 (58) |

EXAMPLE D3 (cont.)

|  | Dose g/ha | 0 | 16 | 32 | 63 | 125 |
|---|---|---|---|---|---|---|
| Cpd F | 0 | — | 10 | 20 | 40 | 60 |
|  | 8 | 10 | 30 (19) | 60 (28) | 65 (46) | 100 (64) |

EXAMPLE D4

Post-emergence treatment of *Digitaria sanguinalis* with various mixtures of Compound F and metribuzin

|  |  | Metribuzin | | |
|---|---|---|---|---|
|  | Dose g/ha | 0 | 16 | 32 |
| Cpd F | 0 | — | 0 | 10 |
|  | 8 | 10 | 20 (10) | 60 (19) |
|  | 16 | 30 | 60 (30) | 70 (37) |

EXAMPLE D5

Post-emergence treatment of *Setaria viridis* with various mixtures of Compound F and metribuzin

|  |  | Metribuzin | | |
|---|---|---|---|---|
|  | Dose g/ha | 0 | 16 | 32 |
| Cpd F | 0 | — | 0 | 20 |
|  | 8 | 0 | 40 | 60 (20) |
|  | 16 | 30 | 60 (30) | 70 (44) |
|  | 32 | 30 | 70 (30) | 80 (44) |
|  | 63 | 45 | 70 (45) | 80 (56) |

According to a further feature of the present invention there are provided herbicidal compositions comprising (a) a 4-benzoylisoxazole derivative of formula I as defined above; and (b) a triazine herbicide;

in association with, and preferably homogeneously dispersed in a herbicidally acceptable diluent or carrier and/or surface active agent.

The term "herbicidal composition" is used in a broad sense, to include not only compositions which are ready for use as herbicides but also concentrate which must be diluted before use. Preferably, the compositions contain form 0.05 to 90% by weight of 4-benzoylisoxazole and triazine herbicide.

Unless otherwise stated, the percentages and ratios appearing in this specification are by weight.

Generally a composition in which the ratio of (a):(b) is from 2:1 to 1:1000 wt/wt is used, proportions of of (a):(b) from 1:3.3 to 1:60 wt/wt being particularly preferred.

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphates. Examples of suitable solid diluents or carriers are aluminium silicate, talc, calcined magnesia, kieselguhr, tricalcium phosphate, powdered cork, absorbent carbon black and clays such as kaolin and bentonite. Examples of suitable liquid diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

The wettable powders (or powders for spraying) usually contain from 20 to 95% of 4-benzoylisoxazole and triazine herbicide, and they usually contain, in addition to the solid vehicle, from 0 to 5% of a wetting agent, from 3 to 10% of a dispersant agent and if necessary, from 0 to 10% of one or more stabilisers and/or other additives such as penetrating agents, adhesives or anti-caking agents and colourings.

The aqueous suspension concentrates, which are applicable by spraying, are prepared in such a way as to obtain a stable fluid product (by fine grinding) which does not settle out and they usually contain from 10 to 75% of 4-benzoylisoxazole and triazine herbicide, from 0.5% to 15% of surface acting agents, from 0.1 to 10% of thixotropic agents, from 0 to 10% of suitable additives such a s antifoams, corrosion inhibitors, stabilisers, and water or an organic liquid in which the active substance is sparingly soluble or insoluble. Some organic solid substances or inorganic salts can be dissolved in order to assist in preventing sedimentation or as antifreeze for the water.

Preferred herbicidal compositions according to the present invention are wettable powders and water-dispersible granules.

Herbicidal compositions according to the present invention may also comprise a 4-benzoylisozaxole and a triazine herbicide in association with, and preferably homogeneously dispersed in, one or more other pesticidally active compounds and if desired one or more compatible pestricidally acceptable diluents and carriers. Preferred herbicidal compositions according to the present invention are those which comprise a 4-benzoylisozaxole and a triazine herbicide in association with other herbicides.

The compositions of the invention may be made up as an article of manufacture comprising a 4-benzoylisoxazole and a triazine herbicide and optionally other pesticidally active compounds as hereinbefore described, and as is preferred, a herbicidal composition as hereinbefore described and preferably a herbicidal concentrate which must be diluted before use, comprising the 4-benzoylisozaxole and triazine herbicide within a container for the aforesaid 4-benzoylisozaxole and triazine or a said herbicidal composition and instructions physically associated with the aforesaid container, setting out the manner in which the aforesaid 4-benzoylisozaxole and triazine or herbicidal composition contained therein, is to be used to control the growth of weeds. The containers will normally be of the types conventionally used for the storage of chemical substances and concentrated herbicidal compositions, which are solids or liquids at normal ambient temperatures, for example cans and drums of plastics materials or metal (which may be internally-lacquered), bottles of glass and plastics materials; and when the contents of the container is a solid, for example a granular herbicidal composition, boxes, for example of cardboard, plastics material, metal or sacks. The containers will normally be of sufficient capacity, to contain amounts of the active ingredients or herbicidal compositions sufficient to treat at least one hectare of ground, to control the growth of weeds therein but will not exceed a size which is convenient for conventional methods of handling. Instructions will be physically associated with the container, for example by being printed directly thereon or on a label or tag affixed thereto. The directions will normally indicate that the contents of the container, after dilution if necessary, are to be applied to control the growth of weeds at rates of application from 5 to 500 g of 4-benzoylisozaxole and from 250 g to 5000 g of a triazine herbicide per hectare in the manner and for the purpose hereinbefore described.

According to a further feature of the present invention, there is provided a product comprising (a) 4-benzoylisozaole of formula I above and (b) a triazine herbicide, as a combined preparation for simultaneous, separate or sequential use in controlling the growth of weeds at a locus.

While the invention has been described in terms of various preferred embodiments, the skilled artisan will appreciate that various modifications, substituitions, omissions, and changes may be made without departing from the spirit thereof. Accordingly, it is intended that the scope of the present invention be limited solely by the scope of the following claims, including equivalents thereof.

What is claimed is:

1. A method for controlling the growth of weeds at a locus, said method comprising applying to said locus a synergistic herbicidally effective amount of:

(a) a 4-benzoylisoxazole having the formula I:

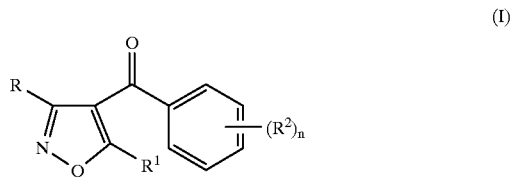

wherein:
R is hydrogen or —$CO_2R^3$;
$R^1$ is cyclopropyl;
$R^2$ is halogen, —$S(O)_pCH_3$, $C_{1-6}$ alkyl or $C_{1-6}$ haloalkyl;
n is two or three;
p is zero, one or two; and
$R^3$ is $C_{1-4}$ alkyl; and (b) a triazine herbicide;
the ratio by weight of (a):(b) being from 2:1 to 1:1000.

2. A method according to claim 1 wherein the triazine herbicide is a compound of formula II:

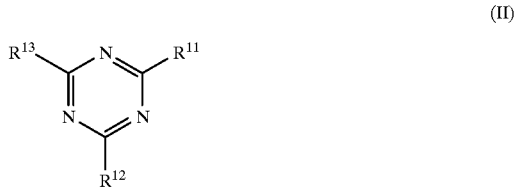

wherein $R^{11}$ represents chlorine or straight- or branched chain alkylthio or alkoxy having from one to six carbon atoms; $R^{12}$ represents azido, monoalkylamino, dialkylamino or cycloalkylamino, in which the alkyl or cycloalkyl moieties are optionally substituted by one or more substituents selected from cyano and alkoxy; and $R^{13}$ represents straight- or branched- chain N-alkylamino having from one to six carbon atoms; or of formula (III)

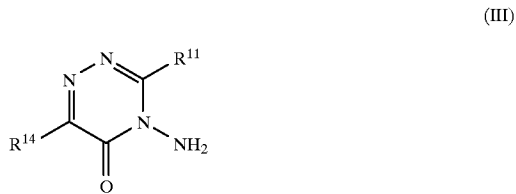

wherein $R^{11}$ is as defined above and $R^{14}$ represents straight- or branched chain alkyl having from one to six carbon atoms.

3. A method according to claim 2 wherein in formula II, $R^{12}$ represents azido or straight- or branched- chain N-alkylamino having from one to four carbon atoms wherein the alkyl moiety is optionally substituted cyano or methoxy.

4. A method according to claim 1 wherein the triazine herbicide is:
simazine, which is 6-chloro-$N^2,N^4$-diethyl-1,3,5-triazine-2,4-diamine;
cyanazine, which is 2-(4-chloro-6-ethylamino-1,3,5-triazin-2-ylamino)-2-methylpropionitrile;

or atrazine, which is 6-chloro-$N^2$-ethyl-$N^4$-isopropyl-1,3,5-triazine-2,4-diamine.

5. A method according to claim 4 wherein the triazine herbicide is cyanazine or atrazine.

6. A method according to claim 1 wherein the triazine herbicide is metribuzin, which is 4-amino-6-tert-butyl-3-methylthio-1,2,4-triazin-5(4H)-one.

7. A method according to claim 1 wherein in formula I, one of the groups $R^2$ is —S(O)$_p$Me and p is as defined in claim 1.

8. A method according to claim 1 wherein in formula I n is three and the groups $(R^2)_n$ occupy the 2,3 and 4-positions of the benzoyl ring; or n is two and the groups $(R^2)_n$ occupy the 2 and 4- positions of the benzoyl ring.

9. A method according to claim 1 wherein in formula I $(R^2)_n$ represents 2-SO$_2$Me-4-CF$_3$, 2-CF$_3$-4-SO$_2$Me, 2-Cl-4-SO$_2$Me, 2-SO$_2$Me-4-Br, 2-SO$_2$Me-4-Cl or 2-SMe-3,4-dichloro.

10. A method according to claim 1 in which the compound of formula I is 5-cyclopropyl-4-(2-methylsulphonyl-4-trifluoromethyl)benzoylisoxazole.

11. A method according to claim 1 in which the compound of formula I is ethyl 3-[5-cyclopropyl-4-(3,4-dichloro-2-methylsulphenyl)benzoylisoxazole]carboxylate.

12. A method according to claim 1 in which the application rate of 4-benzoylisoxazole is from 5 g to 500 g per hectare and the application rate of triazine herbicide is from 250 g to 5000 g per hectare.

13. A method according to claim 1 in which the application rate of 4-benzoylisoxazole is from 25 g to 150 g per hectare and the application rate of triazine herbicide is from 500 g to 1500 g per hectare.

14. A method according to claim 1 wherein of grass weeds in maize are controlled.

15. A method according to claim 1 wherein the compounds are applied pre-emergence of the weeds.

16. A method according to claim 6 wherein the compounds are applied post-emergence of the weeds.

17. A method according to claim 1, wherein the compound of formula I is 5-cyclopropyl-4-(2-methylsulphonyl-4-trifluoromethyl)benzoylisoxazole and the triazine herbicide is atrazine.

18. A method according to claim 1, wherein the compound of formula I is 5-cyclopropyl-4-(2-methylsulphonyl-4-trifluoromethyl)benzoylisoxazole and the triazine herbicide is cyanazine.

19. A method according to claim 1, wherein the compound of formula I is ethyl 3-[5-cyclopropyl-4-(3,4-dichloro-2-methylsulphenyl)benzoylisoxazole]carboxylate and the triazine herbicide is metribuzin.

20. A herbicidal composition comprising:
(i) a synergistic herbicidially effective amount of:

(a) a 4-benzoylisoxazole having the formula I:

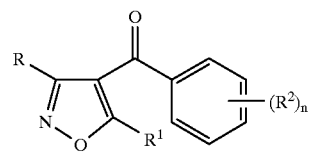

(I)

wherein:
R is hydrogen or —CO$_2$R$^3$;
$R^1$ is cyclopropyl;
$R^2$ is halogen, —S(O)$_p$CH$_3$, $C_{1-6}$ alkyl or $C_{1-6}$ haloalkyl;
n is two or three;
p is zero, one or two; and
$R^3$ is $C_{1-4}$ alkyl; and
(b) a triazine herbicide;
the ratio by weight of (a):(b) being from 2:1 to 1:1000; and
(ii) at least one member selected from the group consisting of a herbicidally acceptable diluent or carrier and a surface-active agent.

21. A composition according to claim 20 wherein the triazine herbicide is a compound of formula II:

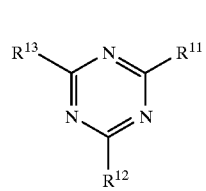

(II)

wherein $R^{11}$ represents chlorine or straight- or branched-chain alkylthio or alkoxy having from one to six carbon atoms; $R^{12}$ represents azido, monoalkylamino, dialkylamino or cycloalkylamino, in which the alkyl or cycloalkyl moieties are optionally substituted by one or more substituents selected from cyano and alkoxy; and $R^{13}$ represents straight- or branched-chain N-alkylamino having from one to six carbon atoms; or of formula (III):

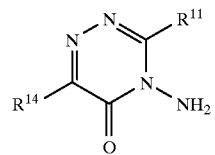

(III)

wherein $R^{11}$ is a defined above and $R^{14}$ represents straight- or branched-chain alkyl having from one to six carbon atoms.

22. A composition according to claim 21 wherein in formula II, $R^{12}$ represents azido or straight- or branched-chain N-alkylamino having from one to four carbon atoms wherein the alkyl moiety is optionally substituted by cyano or methoxy.

23. A composition according to claim 20 wherein the triazine herbicide is:

simazine, which is 6-chloro-$N^2$,$N^4$-diethyl-1,3,5-triazine, 2,4-diamine;

cyanazine, which is 2-(4-chloro-6-ethylamino-1,3-5-triazin-2-ylamino)-2-methylpropionitrile;

or atrazine, which is 6-chloro-$N^2$-ethyl-$N^4$-isopropyl-1,3,5-triazine-2,4-diamine.

24. A composition according to claim 23 wherein the triazine herbicide is cyanazine or atrazine.

25. A composition according to claim 20 wherein the triazine herbicide is metribuzin, which is 4-amino-6-tert-butyl-3-methylthio-1,2,4-triazin-5(4H)-one.

26. A composition according to claim 20 wherein in formula I, one of the groups $R^2$ is —S(O)$_p$Me and p is defined in claim 1.

27. A composition according to claim 20 wherein in formula I n is three and the groups $(R^2)_n$ occupy the 2, 3 and 4-positions of the benzoyl ring; or n is two and the groups $(R^2)_n$ occupy the 2 and 4-positions of the benzoyl ring.

28. A composition according to claim 20 wherein in formula I$(R^2)_n$ represents 2-SO$_2$Me-4-CF$_3$, 2-CF$_3$-4-SO$_2$Me, 2-Cl-4-SO$_2$Me, 2-SO$_2$Me-4-Br, 2-SO$_2$Me-4-Cl or 2-SMe-3,4-dichloro.

29. A composition according to claim 20 in which the compound of formula I is 5-cyclopropyl-4-(2-methylsulphonyl-4-trifluoromethyl)benzoylisoxazole.

30. A composition according to claim 20 in which the compound of formula I is ethyl 3-[5-cyclopropyl-4-(3,4-dichloro-2-methylsulphenyl)benzoylisoxazole]carboxylate.

31. A composition according to claim 20, wherein the compound of formula I is 5-cyclopropyl-4-(2-methylsulphonyl-4-trifluoromethyl)benzoylisoxazole and the triazine herbicide is atrazine.

32. A composition according to claim 20, wherein the compound of formula I is 5-cyclopropyl-4-(2-methylsulphonyl-4-trifluoromethyl)benzoylisoxazole and the triazine herbicide is cyanazine.

33. A composition according to claim 20, wherein the compound of formula I is ethyl 3-[5-cyclopropyl-4-(3,4-dichloro-2-methylsulphenyl)benzoylisoxazole]carboxylate and the triazine herbicide is metribuzin.

34. A herbicidal composition according to claim 20 in which the ratio by weight of (a):(b) is from 1:3.3 to 1:60 wt/wt.

35. A herbicidal combination comprising, in synergistic herbicidally effective amount:

(a) a 4-benzoylisoxazole having the formula I:

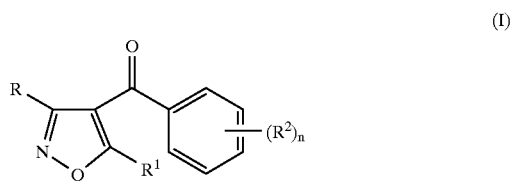

(I)

wherein:
R is hydrogen or —CO$_2$R$^3$;
R$^1$ is cyclopropyl;
R$^2$ is halogen, —S(O)$_p$CH$_3$, C$_{1-6}$ alkyl or C$_{1-6}$ haloalkyl;
n is two or three;
p is zero, one or two; and
R$^3$ is C$_{1-4}$ alkyl; and (b) a triazine herbicide;

the ratio by weight of (a):(b) being from 2:1 to 1:1000.

* * * * *